United States Patent [19]

Reimschuessel et al.

[11] 4,393,233

[45] Jul. 12, 1983

[54] PREPARATION OF P-(1,1-DIMETHYL-2-HYDROXYETHYL)-BENZOIC ACID

[75] Inventors: Herbert K. Reimschuessel, Morristown; Bruce T. DeBona, Madison, both of N.J.

[73] Assignee: Allied Corporation, Morris Township, Morris County, N.J.

[21] Appl. No.: 337,900

[22] Filed: Jan. 7, 1982

Related U.S. Application Data

[62] Division of Ser. No. 153,361, May 27, 1980, Pat. No. 4,310,655.

[51] Int. Cl.$^3$ ............................................. C07C 65/00
[52] U.S. Cl. ...................................... 562/473; 560/64
[58] Field of Search ........................... 562/473; 560/64

[56] References Cited

U.S. PATENT DOCUMENTS

| | | | |
|---|---|---|---|
| 2,552,269 | 5/1951 | Emerson | 560/64 |
| 3,184,468 | 5/1965 | Siegrist et al. | 562/473 |
| 4,218,567 | 8/1980 | Manchand et al. | 560/64 |

*Primary Examiner*—Paul J. Killos
*Attorney, Agent, or Firm*—Alan M. Doernberg; Robert A. Harman

[57] ABSTRACT

The subject polymers are novel homopolymers and copolymers. The homopolymers are characterized by relatively high $T_g$ of about 120° C. relative to their $T_m$ of about 250° C., whereby they can readily be fabricated into fibers, films and like structures from the melt, and retain strength above 100° C. The copolymers have $T_g$'s intermediate between those of the homopolymers of the constituent monomers, and can be fabricated as for the subject homopolymers.

Novel processes of obtaining the monomer, p-(1,1-dimethyl-2-hydroxyethyl)benzoic acid, are disclosed.

2 Claims, No Drawings

PREPARATION OF P-(1,1-DIMETHYL-2-HYDROXYETHYL)BENZOIC ACID

This application is a division of application Ser. No. 153,361, filed May 27, 1980, U.S. Pat. No. 4,310,655.

The new polymers according to the present invention are polyesters that may be obtained by either direct polycondensation of p-(1,1-dimethyl-2-hydroxyethyl)-benzoic acid or by a polytransesterification process employing an alkyl or phenyl ester of this benzoic acid derivative. The free p-(1,1-dimethyl-2-hydroxyethyl)-benzoic acid may be obtained according to the procedure reported by Heck and Winstein in J.A.C.S. 79, 3432 (1957); or more advantageously by methods of this invention. These polymers include homopolymers and copolymers.

BACKGROUND OF THE INVENTION

It is known that hydroxy acids have a potential for the formation of polyesters. For instance, poly(meta-oxybenzoyl) can be derived from m-hydroxybenzoic acid [Gilkey and Caldwell, *J. Appl. Polym. Sci.* 2, 198 (1959)]; and a polyester derived from p-(2-hydroxyethyl)benzoic acid (no methyl side groups) has been reported (Cook, et al., Brit. Pat. No. 604,985, ICI). It appeared therefore conceivable that p-(1,1-dimethyl-2-hydroxyethyl)benzoic acid may also form a polyester. However, we found that the polyester that indeed formed has completely unexpected thermal properties, advantageous for practical purposes, namely a melting point ($T_m$) allowing facile processing on conventional fiber and film melt extrusion equipment, combined with a comparatively high glass transition temperature ($T_g$), high enough to allow uses in which retention of strength at temperatures above 100° C. is important.

SUMMARY OF THE INVENTION

In accordance with this invention, we have devised new procedures for synthesizing the polyesterforming acid, p-(1,1-dimethyl-2-hydroxyethyl)benzoic acid; we have successfully produced polymers thereof, both homopolymers and copolymers with certain polyester-forming compounds; and we have demonstrated unusual and advantageous thermal properties of said homopolymers, namely a melting point of about 250° C. coupled with a glass transition at about 120° C.

It is well known that for most commercially important polymers (of the semicrystalline type) the ratio $T_g/T_m$ is represented by values in the range of 0.5 to 0.8, usually about 0.66 (temperature measured in °K.). For example, polyethylene terephthalate has $T_m$ about 265° C. and $T_g$ about 70°–80° C. giving a $T_g/T_m$ (in °K.) ratio of about 0.64–0.66. The values of $T_m$ and $T_g$ are of particular significance when conventional melt processing is the most desirable operation for obtaining shaped objects such as fibers and films. The upper temperature range for commercial melt processing operations as employed particularly in the manufacture of the principal thermoplastic polymers encompasses temperatures between 250° and 300° C. The specific process temperatures are generally 25° to 50° C. above the melting point of the corresponding polymers in order to assure a tractable polymer melt viscosity. Thus with a $T_g/T_m$ ratio of about 0.66 the corresponding glass transition temperatures are usually in the range of 40° to 80° C. Notwithstanding good general mechanical and physical properties, these polymers accordingly are deficient in applications where strength retention upon exposure to temperatures at or above 100° C. is desired or essential.

The polymer according to the present invention is, therefore, characterized by a most desirable, but unusual, combination of its principal transition temperatures. The melting point in the range of 250° to 253° C. permits, first, a simple polycondensation process in a homogeneous melt system; and second, permits processing in conventional extrusion and spinning equipment. The $T_g/T_m$ ratio, above discussed, is unusually high, about 0.75. The correspondingly high glass transition temperature in the range of 120° to 123° C. makes this polymer suitable for high performance uses (high tensile modulus) such as in tire cords, as well as for applications that encompass intrinsically easy care, wash and wear fabrics, steam sterilizable objects and packaging, particularly that obtained by thermoforming.

The properties of our new polyester can be modified by either blending it with another polymer or incorporating other structural segments. The latter, as we have demonstrated, is readily achieved by copolymerization of the p-(1,1-dimethyl-2-hydroxyethyl)benzoic acid with other hydroxy acids, including diacid/diol condensates such as, specifically, 2-hydroxyethyl terephthalate. In its broad aspects, our generally employed processes for production of polymers of (p-1,1-dimethyl-2-hydroxyethyl)benzoic acid and its polymerization products comprise the steps:

(1) Brominating isobutyric acid;

(2) Condensing the resulting alpha-bromoisobutyric acid with benzene;

(3) Brominating the resulting dimethylphenylacetic acid;

(4) Reducing the carboxyl group of the brominated acid obtained in step (3) to form p-(1,1-dimethyl-1-hydroxyethyl)bromobenzene;

(5) Replacing the bromine atom in the product obtained in step (4) by the cyano group;

(6) Converting the cyano group in the product of step (5) to the carboxyl group;

(7) Condensing intermolecularly, hydroxy and carboxyl groups of the product of step (6).

An alternative process comprises the steps:

(1) p-Acetylating beta, beta-dimethylphenethyl acetate;

(2) Oxidizing the acetyl group in the product of step (1) to carboxyl and converting the ester group to hydroxyl, to form (p-1,1-dimethyl-2-hydroxyethyl)benzoic acid;

(3) Condensing, intermolecularly, hydroxy and carboxyl groups of the product of step (2).

In the following are presented examples on:

(1) The reaction scheme and approaches practiced for the synthesis of p-(1,1-dimethyl-2-hydroxyethyl)benzoic acid.

(2) Polymer synthesis.

(3) Synthesis of copolymers.

These examples are given for the purpose of illustration and demonstration and not by way of limitation.

(A) MONOMER SYNTHESIS

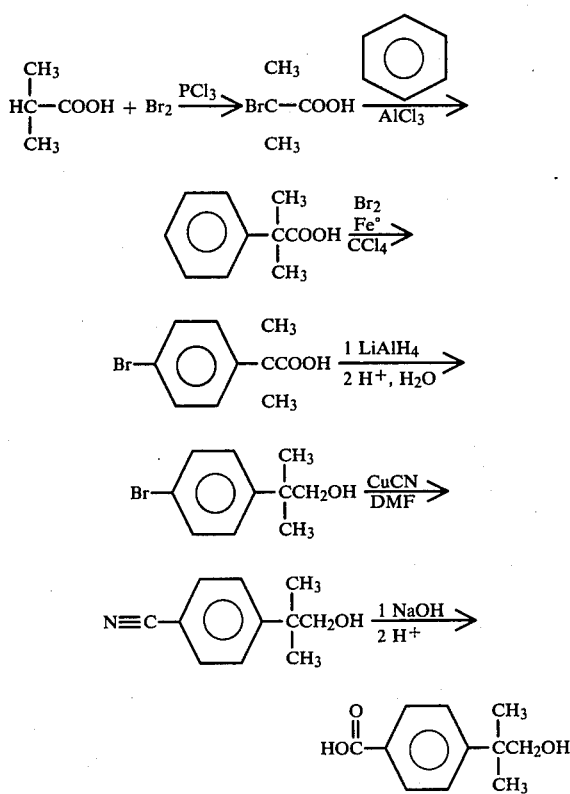

ALPHA-BROMOISOBUTYRIC ACID

Pure dry isobutyric acid 264.3 g, 3 moles, was placed in a 3-necked flask fitted with a reflux condenser, drying tube, dropping funnel, thermometer and magnetic stirring bar. The flask was then heated to ca. 80° C. by means of an oil bath and $PCl_3$, 5.2 mL, was added rapidly through the condenser. Dry bromine 168 mL, 3.28 moles, was then added dropwise at such a rate that the temperature of the mixture remained at about 80° C. The addition took about 1.5 hrs. The reaction mixture was then maintained at 70°–80° C. with stirring for 18 hours; and finally at 100° C. for ½ hour.

The crude alpha-bromoisobutyric acid was then distilled with the aid of a water aspirator. A redistillation using a mechanical pump at 12–15 torr (1.6–2.0 kPa) gaves a purified product, bp 103°–105° C., m.p. 38°–43° C. The yield of redistilled material was about 66%.

Elem. Anal. ($C_4H_7BrO_2$) Calc: % C=28.8; % H=4.2; % Br=47.9. Found: % C=28.6; % H=4.1; % Br=47.2.

NMR spectrum (in $CDCl_3$): 1.98 δ (singlet) $CH_3$; 12.23 δ (singlet) COOH; in ratio 6:1.

DIMETHYLPHENYLACETIC ACID

Molten alpha-bromoisobutyric acid, 328 g, 2 moles, was added to a 5-L flask equipped with a reflux condenser and large magnetic stirrer. Anhydrous benzene 2000 mL, was added to the flask, followed by fresh anhydrous $AlCl_3$, 900 g, 6.75 moles, in small portions. The solution was then slowly heated to the reflux temperature and at this time the exit of the reflux condenser was connected to a flowing-water HBr trap. The mixture was heated a total of 24 hours without interruption.

The reaction mixture was then cooled to ca. 5° C. and treated with 2 L of 50/50 (by volume) conc. $HCl/H_2O$ to decompose the catalyst complex. The benzene layer was then separated, washed once with ice-cold $H_2O$ (1200 mL) and twice with dilute aqueous sodium hydroxide. The aqueous sodium hydroxide extracts were combined, heated to 80° C. to drive out any physically trapped benzene and decolorized with activated charcoal. After filtration through diatomaceous earth filter aid ("Celite") the aqueous basic filtrate was neutralized slowly with conc. HCl. The precipitated acid was filtered, washed with a minimum amount of ice-cold water, and dried in a vacuum oven at 25°–30° C. The crude yield was 209 g (65%), and the melting point at this stage was 75.5°–77° C. The crude acid was recrystallized from n-heptane (450 mL for ca. 200 g acid). The final yield was 180 g of mp=76°–78°.

Elem. Anal. ($C_{10}H_{12}O_2$) Calc: % C=73.1; % H=7.37. Found: % C=73.1; % H=7.48.

NMR ($CDCl_3$): 1.53 δ (singlet) $CH_3$; 7.30 δ (multiplet) phenyl; 11.95 δ (singlet) COOH; in ratio 6:5:1.

DIMETHYL(P-BROMOPHENYL)ACETIC ACID

Dry dimethylphenylacetic acid, 152 g. 0.926 mole, was added to a flask equipped with a reflux condenser, magnetic stirrer and oil bath. A solution of bromine, 50 mL, 0.97 mole, in dry carbon tetrachloride (172 mL) was then added along with iron metal "filings," 0.23 g. The mixture was gently refluxed for 16 hours and cooled to ca. 35° C. whereupon material began to crystallize out of solution. Enough carbon tetrachloride (ca. 300 mL) was then added to redissolve the crystals and the solution was washed with ca. 500 mL of dilute aqueous $H_2SO_4$, followed by 500 mL of water. The washed $CCl_4$ solution was extracted with 10% aqueous NaOH. The combined basic extracts were washed with petroleum ether or pentane to remove $CCl_4$ and then neutralized at 0° C. with aqueous $H_2SO_4$ (50%). The precipitated crude acid was collected on a filtering funnel, washed with cold water and vacuum dried at 40° C. The crude yield was 220 g (98%), mp=106°–116° C. Four recrystallizations from methanol-water (50/50 vol) gave a final mp of 122°–124° C.

Elem. Anal. ($C_{10}H_{11}BrO_2$) Calc: % C=49.4; % H=4.56; % Br=32.9. Found: % C=49.5; % H=4.63; % Br=32.4.

NMR ($CDCl_3$) 1.52 δ (singlet) $CH_3$; 7.15 to 7.55 (AA'BB') phenyl; 11.35 δ (singlet) COOH; in ratio 6:4:1.

P-(1,1-DIMETHYL-2-HYDROXYETHYL)BROMOBENZENE

Lithium tetrahydridoaluminate, 29 g, 0.764 mole, was added to 1500 mL of dry ether in a 5-L flask equipped with a heating mantle, reflux condenser, dropping funnel, mechanical stirrer and guard tube. The slurry was stirred for about 20 to 30 minutes, and then a solution of dimethyl-p-bromophenylacetic acid, 165 g, 0.679 mole, in 600 mL of dry ether was added dropwise at a rate sufficient to maintain gentle reflux. The addition required about 2.5 hours. The mixture was then maintained at reflux for an additional hour.

The heating mantle was replaced by an ice-water bath and the mixture cooled to 0° to 5° C. About 1500 mL of cold conc. $HCl/H_2O$ (50/50 vol.) was added very carefully dropwise to decompose unreacted hydridoaluminate and aluminum salts. The two layers were separated and the ether layer was washed once with 500 mL water and once with 500 mL of 5% aqueous sodium bicarbonate. The ether layer was finally dried over anhydrous potassium carbonate. Removal of the ether in a rotoevaporator left a liquid which crystallized upon cooling to room temperature. The yield of crude alcohol was 148.3 g (95%), mp 43°–46° C. This crude product was recrystallized from pentane to give colorless crystals melting at 46.5°–48° C.

Elem. Anal. ($C_{10}H_{13}BrO$) Calc: % C=52.4; % H=5.72; % Br=34.9. Found: % C=52.3; % H=5.97; % Br=34.4.

NMR ($CDCl_3$) 1.21 δ (singlet) $CH_3$; 1.56 δ (singlet OH; 3.45 δ (singlet) $CH_2$; 7.10 to 7.50 δ (AA'BB') phenyl; in ratio 6:1:2:4.

P-(1,1-DIMETHYL-2-HYDROXYETHYL)CYANOBENZENE p-(1,1-Dimethyl-2-hydroxyethyl)bromobenzene, 148 g, 0.646 mole, was added to a 1 L flask fitted with a reflux condenser, magnetic stirrer and oil bath. Dimethylformamide, 350 mL, and cuprous cyanide, 69.4 g, 0.775 mole were then added to the flask. The heterogeneous mixture was heated to gentle reflux whereupon it became somewhat more homogeneous and would then easily stir. The mixture was heated at reflux for five hours. While still hot the mixture was cast into 1 L of water using 100 mL of hot DMF for washing out the flask. The precipitated residue was stirred by hand as well as possible, allowed to settle and the greater portion of the water decanted and discarded. A freshly prepared solution of ferric chloride, 340 g; conc. HCl, 85 mL; water, 510 mL was added to the residue to destroy copper complexes. The mixture was heated with good stirring at 60° to 70° C. for 20 to 30 minutes. The crude nitrile was then extracted with three 200 mL portions of benzene. The benzene extracts were combined and dried over anhydrous $K_2CO_3$ for ½ hour. Benzene was removed in a rotoevaporator to give a yellowish oil which crystallized easily when cooled to room temperature and scratched. The yield was about 102 g (90%), mp=70°–82° C.

The product was recrystallized as follows: The crude material was dissolved in about 100 mL of $CCl_4$ and the resultant solution was decolorized with activated charcoal. To the filtered solution about 400 mL of n-heptane was added, then the solution was heated back to the reflux point. The cyanoalcohol crystallized upon cooling to room temperature, mp=84°–85° C.

Elem. Anal. ($C_{11}H_{13}NO$) Calc: % C=75.4; % H=7.48; % N=7.99. Found: % C=75.4; % H=7.46; % N=7.77.

The mass, IR and NMR spectra were consistent with the proposed structure.

P-(1,1-DIMETHYL-2-HYDROXYETHYL)BENZOIC ACID p-(1,1-Dimethyl-2-hydroxyethyl)cyanobenzene, 75 g, 0.43 mole, was dissolved in a solution of ethylene glycol, 150 mL, and water, 50 mL, at 80° C. in a 2-L flask. The above solution was then heated on an oil bath with good stirring to 135°–140° C. A solution of 50% aqueous NaOH, 140 mL, in 150 mL water was added dropwise at such a rate that a gentle reflux was maintained, and the resulting clear solution was allowed to reflux until no more ammonia could be detected The solution was then diluted while still hot with 500 mL water and then allowed to cool to room temperature. The cooled solution was extracted twice with 100 mL portions of ether and the ether layers discarded. The aqueous layer was heated on a steam bath to expel any trapped ether, cooled to 0° C. and acidified with conc. HCl. The precipitated hydroxyacid was filtered, washed with 150 mL ice-cold water and dried in a vacuum oven at 50° C. The crude yield was 80 g (96%), mp=154°–156° C. The material was recrystallized once from water/methanol (3/1 vol.) ca. 1100 mL and three more times from boiling water. The final mp=156°–157° C. vs. 158°–159° C. (Heck et al., above).

Elem. Anal. ($C_{11}H_{14}O_3$) Calc: % C=68.0; % H=7.26. Found: % C=68.0; % H=7.21.

NMR ($CD_3COOH$): 1.38 δ (singlet) $CH_3$; 3.78 δ (singlet) $CH_2$; 7.58 to 8.24 δ (AA'BB') phenyl, in ratio of 6:2:4.

Neutralization Equivalent=194.41 (theory=194.22).

IR spectrum (KBr pellet)-wave numbers: 1685 (C=O); 2520 and 2645 (OH of COOH); 1280 (C—O); 1360 and 1382 (gem—$CH_3$).

Mass spectrum showed m/e peaks ($CH_4/NH_3$ probe) at 177 $M+H^+ - H_2O$; 195 $M+H^+$; 212 $M+NH_4^+$.

(B) ALTERNATIVE MONOMER SYNTHESIS

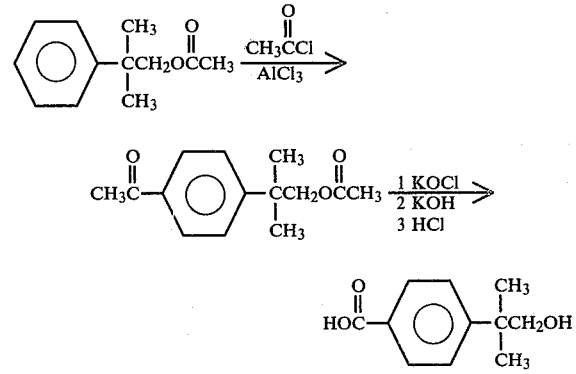

β,β-dimethylphenethyl acetate was prepared and purified by the method described in U.S. Pat. No. 3,378,578. To a 3-L reaction flask equipped with mechanical stirrer, reflux condenser, drying tube, thermometer and dropping bottle was added 300 g anhydrous aluminum chloride dissolved in 900 mL anhydrous dichloromethane. Acetal chloride, 300 g, was added rapidly dropwise with good stirring and the temperature controlled to 10° C. by means of a water-ice bath. The beta,beta-dimethylphenethyl acetate, 156 g, dissolved in 300 mL dichloromethane was then added dropwise at such a rate that the temperature remained at 2° C. throughout the addition. The reaction mixture was stirred for an additional 15 minutes, whereupon it was poured carefully over 600 g of crushed ice. The organic layer was separated, washed twice with 250 mL of 5% aqueous HCl, twice with 250 mL of 5% aqueous sodium bicarbonate and then with water until neutral. The organic solution was then dried over anhydrous sodium sulfate and the solvent removed on a rotoevaporator at temperatures not exceeding over 50° C. The crude yield was 173 g. This crude product was then distilled to give material of acceptable purity for characterization, bp 120°–130° C. at 0.5 to 0.6 torr (0.0665–0.0798 kPa). A 60 $MH_z$ NMR spectrum was obtained with $CDCl_3$ as solvent; 1.36 δ singlet (gem—$CH_3$), 1.95 δ singlet ($CH_3$ ester), 2.55 δ singlet ($CH_3$ ketone), 4.15 δ singlet ($CH_2$), 7.37 to 7.98 δ "quartet" (phenyl). The integration ratio was 6:3:3:2:4 as expected from the proposed structure. The infrared spectrum was also consistent with the proposed structure.

The purified p-acetyl(1,1-dimethyl-2-acetoxyethyl)-benzene was converted to the desired monomer, i.e. p-(1,1-dimethyl-2-hydroxyethyl)benzoic acid by oxidation with aqueous hypochlorite followed by saponification and acidification as follows: Freshly prepared aqueous potassium hypochlorite (1.5 L, ca. 2 moles) was placed in a 3-L flask equipped with a mechanical stirrer, reflux condenser, thermometer and oil bath. The solution was warmed to 35° C., whereupon the above described ketone (83 g) was added in a single portion. The reaction temperature was increased to 70° C. over a two hour period with vigorous stirring. The mixture was stirred vigorously at 70° C. for an additional 2.5 hours, cooled to room temperature and excess hypochlorite decomposed with 250 mL of 20% aqueous sodium metabisulfite. A small sample of the reaction mixture was tested for hypochlorite with acidified potassium iodide.

The reaction mixture was then washed with three 150 mL portions of ether and the aqueous phase saponified with potassium hydroxide (40 g) at reflux for three hours. The resultant clear solution was cooled and acidified with conc. HCl. The precipitated crude product was washed with cold water and dried. The yield was 35 g, mp 150° C. The product could be further purified by the technique mentioned previously to give an ultimate mp of 156° C. The material is identical to that obtained by the first method as shown by NMR, IR, elem. anal. A mixed melting point showed no depression.

P-(1,1-DIMETHYL-2-HYDROXYETHYL)BENZOIC ACID METHYL ESTER

The following reagents were placed in a flask equipped with a magnetic stirrer, oil bath and reflux condenser protected with a guard tube containing anhydrous calcium sulfate ("Drierite"): p-(1,1-dimethyl-2-hydroxyethyl)benzoic acid, 20 g, 0.103 mole; sodium bicarbonate, 9.4 g, 0.112 mole; N,N-dimethylacetamide, 100 mL; and methyl iodide, 28.4 g, 0.2 mole. The mixture was heated at 80° C. for 2.5 hours, cooled to room temperature and filtered to remove any unreacted hydroxyacid. The clear solution was then poured into 600 mL water and stirred for 10 minutes. 50 mL of 5% aqueous sodium bicarbonate was added and the resultant solution extracted 3 times with 120 mL portions of ether. The ether layers were combined, washed with dilute aqueous bicarbonate, dilute aqueous sodium thiosulfate and finally water, and dried over anhydrous potassium carbonate. The ether solution was evaporated to give a colorless liquid which crystallized upon standing at room temperature. Yield 99%. The compound was purified by distillation, bp 135°–140° C. at 0.3 to 0.5 mm Hg, (0.04 to 0.667 kPa) followed by recrystallization from ether/pentane (¼ vol.) at −20° C., mp 44°–45° C. Elemental analysis, IR and NMR spectra were all consistent with the proposed structure.

POLYCONDENSATION

EXAMPLE 1

Poly(p-1,1-dimethyl-2-oxyethylbenzoyl) [from hydroxyacid]

The below cited melt polycondensations were conducted essentially as follows (using in most instances the monomer obtained by Procedure (A) above).

A 30 mL polymerization tube equipped with a glass capillary tube reaching to the bottom, and with a side arm, was charged with 9 g of the monomer containing 0.002 g antimony triacetate as catalyst. The tube was then placed in a vapor bath at 222° C. (methyl saliycylate) and after the monomer had melted, nitrogen gas flow was applied to the capillary. After a few minutes vacuum was applied to the side arm gradually over a 25 minute period. The final pressure was 1 to 3 torr (0.133–0.40 kPa). These conditions were maintained for one hour whereupon the tube was then transferred to a vapor bath at 275° C. (triethylene glycol) without interruption of inert gas flow or vacuum. The pressure was lowered to 0.5–1.0 torr (0.0667–0.133 kPa) and the conditions maintained for 3 hours. The tube was then removed from the bath and allowed to cool either slowly under vacuum or quenched rapidly in cold water.

The polymer which was isolated as a hard glassy plug is soluble in many solvents among which are α-methylnaphthalene, hexafluoroisopropanol, phenol/symtetrachloroethane (60/40 wt) and trifluoroacetic acid, and can be purified by the usual precipitation techniques with ethanol as the non-solvent. The viscosity number of the above polymer was 40 mL/g (in phenol/tetrachloroethane (60/40 by wgt) at 0.5 g/100 mL concentration and 25° C.).

The elemental analysis of the above precipitated polymer was in agreement with the theoretical repeat unit: $(C_{11}H_{12}O_2)_n$ Calc: % C=75.0; % H=6.86. Found: % C=74.7; % H=7.00.

The IR (film cast from hexafluoroisopropanol) as well as NMR (in trifluoroacetic acid) spectra were consistent with the proposed polymer structure. IR-wave numbers: 2980 (aliphatic $CH_3$); 1720 (C=O of ester); NMR: broad peaks but otherwise identical to monomer-rel. to tms: 1.50 δ (singlet) $CH_3$; 4.55 δ (singlet) $CH_2$; 7.56 to 8.10 δ (AA'BB') phenyl; with ratio of 6:2:4.

The structure of the polymer was further confirmed by saponification back to monomer in refluxing 3 N 50/50 aqueous alcoholic potassium hydroxide. The monomer was isolated from the hydrolyzate by acidification with dilute HCl. A mixed melting point with authentic pure monomer showed no depression in the melting point and the NMR spectrum was identical to that of the authentic sample.

Strong fibers could be pulled quite easily from the melt, and tough transparent films could be cast from hexafluoroisopropanol.

Thermal and $T_g$ data: $T_g$=118°–123° by DSC, $T_m$=250° by DSC, 250° by microscopy.

EXAMPLE 2

Polymer was also prepared as in the above example without addition of any catalyst. In this case the viscosity number was 33 mL/g; otherwise the material appeared identical in all respects to that prepared with antimony triacetate as catalyst.

EXAMPLE 3

Poly(p-1,1-dimethyl-2-oxyethylbenzoyl) [from methyl ester]

p-(1,1-dimethyl-2-hydroxyethyl)benzoic acid methyl ester (5 g) was charged into a small polymerization tube equipped with an inlet tube and with a side arm connected to a small vacuum trap. Distilled tetra-n-butyl orthotitanate (0.005 g) was added as catalyst through the inlet tube as a 10% solution in chloroform. With the system vented to the atmosphere through an oil bubbler, argon gas was admitted to the inlet tube and allowed to purge the reaction tube for one-half hour. The monomer was then melted in a Wood's metal bath at 120° to 150° C. with moderate argon flow. These conditions were maintained until no more methanol collected in the trap (about 1.5 hours). The temperature was then slowly raised to 250° C. over a two hour period during which time the material became more viscous. These conditions were maintained for an additional hour. Without interruption of heat or argon flow, the oil bubbler was removed and the system evacuated slowly down to about 2 torr (0.266 kPa). The temperature was then raised to 260°-265° C., and after a few minutes the pressure was lowered to 0.5 torr (0.0667 kPa) by decreasing the argon flow rate. After 1.5 hours under these conditions, the temperature was raised to 270°-280° C. and maintained for ½ hour. At this point, the contents of the tube was so viscous that it would hardly flow.

The tube was removed from the bath and allowed to cool slowly under vacuum (behind a shield). There was obtained about 3 g of extremely hard and transparent polymer in the form of a plug which was almost water white. The viscosity number was 80 mL/g (phenol/TCE, 0.5 g/100 mL).

EXAMPLE 4

Polymer was also prepared from the methyl ester as in the above example without the use of any catalyst; however, longer condensation times were required and materials of lower viscosity numbers resulted.

EXAMPLES 5–9

Copolymers with p-(2-hydroxyethoxy)benzoic acid ester

A mixture of p-(1,1-dimethyl-2-hydroxyethyl)benzoic acid methyl ester (2.12 g) and p-(2-hydroxyethoxy)benzoic acid methyl ester (6.26 g) was placed in a polymerization tube constructed as in the previous example. A solution of 0.0084 g of tetra-n-butyl orthotitanate as catalyst in 0.1 mL chloroform was added and the temperature slowly raised to 220° C. with continuous argon flow over a 3 hour period. The temperature was then raised to 250° C. and the system evacuated to 0.7 mm Hg (0.093 kPa). These conditions were maintained for one hour, whereupon the temperature was raised to 280° C. and the pressure adjusted to 0.4 mm Hg (0.0532 kPa). After 1.5 hours, the reaction was terminated. The copolymer was then dissolved in trifluoroacetic acid (10% solution) and precipitated into 10 volumes of methanol. The white polymer solid was washed with methanol and dried in a vacuum oven. Yield 6.1 g, viscosity number 32 mL/g, (C=0.5 g/100 mL in phenol-TCE).

The same technique was used to prepare other copolymer compositions of these monomers. The copolymer compositions were determined by proton NMR spectroscopy with CF$_3$COOD as solvent. The following Table 1 shows the monomer feed composition, copolymer composition, viscosity numbers and T$_g$ (by DSC) for the copolymers, which can be represented by the structure:

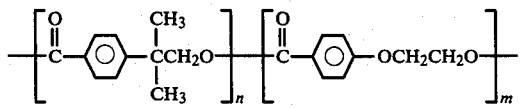

TABLE 1

| Monomer Feed Ratio n/m + n (mole) | Copolymer Ratio n/m + n (mole) | Viscosity Number mL/g(Phenol/ TCE, 0.5%) | Tg (°C.) (DSC, reheat) |
|---|---|---|---|
| Ex. 5 0 | 0 | 70 | 70 |
| Ex. 6 0.24 | 0.31 | 32 | 77 |
| Ex. 7 0.49 | 0.51 | 38 | 87 |
| Ex. 8 0.75 | 0.62 | 61 | 100 |
| Ex. 9 1.00 | 1.00 | 45 | 118 |

EXAMPLES 10–15

Copolymers with bis(2-hydroxyethyl) terephthalate

A mixture of p-(1,1-dimethyl-2-hydroxyethyl)benzoic acid methyl ester (2.05 g, 0.01 mole) and bis(2-hydroxyethyl) terephthalate (8.04 g, 0.032 mole) was placed in a polymerization tube along with 0.0383 g of tetra-n butyl orthotitanate in chloroform. The polymerization was then conducted as described for the previous copolymer example. The yield of copolymer (copolymers of p-(1,1dimethyl-2-hydroxyethyl)benzoic acid and 2-hydroxyethyl terephthalate) after precipitation from trifluoroacetic acid solution in methanol was 6 g; viscosity number 79 mL/g (C=0.5 g/100 mL, phenol/TCE). Other copolymer compositions were prepared in a similar manner. The results are presented in Table 2 below wherein the "n" units are as for Table 1 and the "m" units are from the terephthalate.

TABLE 2

| Monomer Feed Ratio n/m + n (mole) | Copolymer n/m + n (mole) | Viscosity Number mL/g(Phenol/ TCE, 0.5%) | Tg, °C. |
|---|---|---|---|
| Ex. 10 0 | 0 | 0.90 | 70 |
| Ex. 11 0.24 | 0.24 | 0.79 | 80 |
| Ex. 12 0.23 | 0.23 | 1.53 | 80 |
| Ex. 13 0.45 | 0.42 | 1.32 | 86 |
| Ex. 14 0.65 | 0.64 | 0.90 | 95 |
| Ex. 15 0.83 | 0.80 | 0.97 | 104 |
| Ex. 9 1.00 | 1.00 | 0.45 | 118 |

The above copolymers of Examples 6–8 and 11–15 can be formed into useful films, e.g. by casting from solution in a solvent such as hexafluoroisopropanol by broadly known procedure.

We claim:
1. Process for production of (p-1,1-dimethyl-2-hydroxyethyl)benzoic acid comprising the steps:
   (a) Brominating isobutyric acid;
   (b) Condensing the resulting alpha-bromoisobutyric acid with benzene;
   (c) Brominating the resulting dimethylphenylacetic acid;

(d) Reducing the carboxyl group of the brominated acid obtained in step (c) to form p-(1,1-dimethyl-1-hydroxyethyl)bromobenzene;

(e) Replacing the bromine atom in the product obtained in step (d) by the cyano group;

(f) Converting the cyano group in the product of step (e) to the carboxyl group.

2. Process for production of (p-1,1-dimethyl-2-hydroxyethyl)benzoic acid comprising the steps:

(a) p-Acetylating beta,beta-dimethylphenethyl acetate;

(b) Oxidizing the acetyl group in the product of step (a) to carboxyl and converting the ester group to hydroxyl, to form (p-1,1-dimethyl-2-hydroxyethyl)benzoic acid.

* * * * *